United States Patent [19]

Blackman et al.

[11] Patent Number: 5,440,068

[45] Date of Patent: Aug. 8, 1995

[54] ACETONITRILE PURIFICATION VIA AN ADSORPTION-BASED PROCESS

[75] Inventors: Marc W. Blackman, Lyndhurst; Mark C. Cesa, South Euclid; Thomas G. Attig, Aurora, all of Ohio

[73] Assignee: The Standard Oil Company, Cleveland, Ohio

[21] Appl. No.: 176,369

[22] Filed: Dec. 30, 1993

[51] Int. Cl.[6] ............................................. C07C 253/34
[52] U.S. Cl. ....................................................... 558/435
[58] Field of Search .......................................... 558/435

[56] References Cited

U.S. PATENT DOCUMENTS

| | | | |
|---|---|---|---|
| 2,107,904 | 2/1938 | Pool | 558/435 |
| 3,322,814 | 5/1967 | Iappelli | 558/435 |
| 4,105,688 | 8/1978 | Arni et al. | 558/435 X |
| 4,119,497 | 10/1978 | Ocampo et al. | 558/435 X |
| 4,287,134 | 9/1981 | Smiley | 260/465.1 |
| 5,250,721 | 10/1993 | Cesa et al. | 558/435 |

FOREIGN PATENT DOCUMENTS

| | | |
|---|---|---|
| 1002441 | 2/1991 | Belgium . |
| 217212 | 1/1985 | Germany . |
| 3334321 | 4/1985 | Germany . |
| 225692 | 8/1985 | Germany . |
| 229274 | 10/1985 | Germany . |
| 243492 | 3/1987 | Germany . |
| 282818 | 9/1990 | Germany . |
| 5132518 | of 0000 | Japan . |
| 5382722 | of 0000 | Japan . |
| 0082722 | 7/1978 | Japan .................. 558/435 |
| 2249308 | 5/1992 | United Kingdom . |
| 1318588 | 6/1987 | U.S.S.R. . |
| 1318588 | 6/1987 | U.S.S.R. ............... 558/435 |
| WO93/23366 | 11/1993 | WIPO .................. 558/435 |

OTHER PUBLICATIONS

Braunitzer et al., Hoppe-Seyler's Z. Physiol. Chem., 1982, 363(5), pp. 485–486. Only considered in foreign language form.
Carlsen et al., *Analyt. Chem.*, 1979, 51(9), pp. 1593–1595.
Hofmanova et al., (CA 88:179367s), 1978 Considered solely thru submitted abstract.
Kahn et al., *J. Am. Chem. Soc.*, 1988, 110, pp. 7529–7534.
Pavel et al., Chem. Tech. (Leipzig), 1985, 47(8), pp. 328–330. Only considered in foreign language form.
Perrin et al., Purification of Laboratory Chemicals, 2nd Ed., Pergamon Press, NY 1980, pp. 79–81.
Walter et al., Analyt. Chem., 1973, 45(1), pp. 165–166.

*Primary Examiner*—Joseph Paul Brust
*Attorney, Agent, or Firm*—Michael F. Esposito; David P. Yusko; David J. Untener

[57] ABSTRACT

This invention relates to acetonitrile purification via an adsorption-based process. The process comprises pretreating the acetonitrile containing organic impurities such as unsaturated nitriles with a solid reagent to selectively convert the unsaturated nitriles into products more easily removed and passing the treated acetonitrile through a series of adsorbent beds to remove the resulting products and other impurities present from the acetonitrile.

16 Claims, No Drawings

ACETONITRILE PURIFICATION VIA AN ADSORPTION-BASED PROCESS

BACKGROUND OF THE INVENTION

1. Field of the Invention

This invention relates to acetonitrile purification via an adsorption-based process. More particularly, this invention relates to a process for acetonitrile purification involving pretreating the acetonitrile to selectively convert unsaturated nitriles contained in the acetonitrile into products that can be preferentially eliminated. The pretreatment is followed by adsorption to remove the resulting products and other organic impurities present in the acetonitrile.

The acetonitrile purification process of the present invention can be used to up-grade acetonitrile presently produced by chemical plants to a higher purity material of significantly greater value. Specifically, removal of UV-absorbing organic impurities from acetonitrile results in a product with unusually high transparency in the UV and removal of water makes acetonitrile useful in certain commercial applications.

DESCRIPTION OF THE PRIOR ART

Commercial acetonitrile typically contains water as well as trace amounts of acrylonitrile, crotononitrile, acetamide, and allyl alcohol. Applications for high-purity acetonitrile require a UV cutoff of less than 190 nm as well as extremely dry material ($[H_2O] < 1$ ppm). The presence of organic impurities containing $C=C$ and $C=O$ functionalities, which absorb light in the 190–230 nm region, results in the acetonitrile having a UV cutoff above 200 nm. This renders the acetonitrile material unacceptable, therefore requiring further processing by the producers of high-purity acetonitrile. The traditional commercial method of acetonitrile purification utilizes a costly multi-step process involving permanganate oxidation, acid treating, phosphorous pentoxide drying, and two distillations.

Classical methods for purification of acetonitrile are summarized in D. D. Perrin, W. L. F. Armarego, and D. R. Perrin, *Purification of Laboratory Chemicals*, 2nd Ed., Pergammon Press, New York, 1980, pp.79–81. Water is removed by treating acetonitrile with silica gel, 4A molecular sieves, calcium hydride, or phosphoric anhydride, and distilling. Acetic acid and other carboxylic acids can be removed with alumina followed by distillation. Unsaturated nitriles can be removed by initial refluxing with a small amount of aqueous potassium hydroxide solution. However, this reference discloses that preliminary treatment of acetonitrile with cold, saturated aqueous potassium hydroxide is undesirable because of base-catalyzed hydrolysis and the introduction of water. Unsaturated impurities present in the acetonitrile can be removed by treating the acetonitrile with alkaline potassium permanganate solutions but then further treatment to remove water is necessary.

In L. Carlsen, H. Egsgaard, J. J. Andersen, *Analyt. Chem.*, 1979, 51(9), 1593-5, an acetonitrile purification process of treatment with strong base, flash distillation, treatment with a strong acid, fractional distillation, and drying with alumina is disclosed. In A. Hofmanova, K. Angelis, *Chem. Listy*, 1978, 72(3), 306–9, (CA 88:179367s), acetonitrile is purified by boiling for 5 hours with 10% aqueous potassium hydroxide solution, adsorbing on aluminum oxide to remove carboxylic acid salts, drying with phosphoric anhydride or molecular sieve, then fractional distillation from phosphoric anhydride. These methods require multiple steps and involve the use of aqueous base solutions and subsequent distillations and other treatment to remove water and to achieve satisfactory purity.

H. Yu, Z. Xu, in *Shengwu Huaxue Yu Shengwu Wuli Jinzhan*, 1984, 55, 70–2 (CA 100: 127264c) describe treatment of acetonitrile with potassium permanganate-sodium hydroxide in methanol, followed by adsorption by passing through activated charcoal and acidified alumina. In Russia Patent SU 1,318,588, acetonitrile is passed through potassium permanganate adsorbed on alumina to reduce allyl alcohol concentrations to 4–6 ppm and acrylonitrile to 1–3 ppm. These references which disclose the use of potassium permanganate either do not disclose the removal of water after potassium permanganate treatment or involve cumbersome distillations, or require co-treatment with potassium permanganate and a strong base.

The main obstacle to effectively using adsorption for acetonitrile up-grading is the similarity in physical properties between acetonitrile and the unsaturated nitriles contained in the acetonitrile. In order for adsorption to be a viable approach to purification, the unsaturated nitriles must first be converted to other species having sufficiently different physical characteristics.

It is desirable to find a method for acetonitrile purification which does not utilize a costly and cumbersome multi-step process involving distillation.

SUMMARY OF THE INVENTION

It is an object of the present invention to provide a method for acetonitrile purification utilizing adsorption-based technology to produce high-purity acetonitrile.

It is a further object to convert difficult-to-remove impurities such as unsaturated nitriles into more easily removed products such as oxygenates, aromatics, and polymers.

It is another object of this invention to provide an acetonitrile purification process using low cost processing equipment and materials, and having an overall processing cost significantly less than that incurred using traditional distillation-based technology.

It is still another object of the present invention to provide a method for acetonitrile purification which allows for flexibility in process design.

These and other objects, together with the advantages over known methods, shall become apparent from the specification which follows and accomplished by the invention as hereinafter described and claimed.

To achieve the foregoing objects in accordance with the purpose of the invention as embodied and broadly described herein, there is provided a method for acetonitrile purification using an adsorption-based process. The invention is directed to a process for purifying acetonitrile containing impurities comprising unsaturated nitriles and other materials with $C=C$ and $C=O$ functional groups. The process is comprised of the steps of pretreating the acetonitrile by adding a solid reagent to selectively convert the unsaturated nitriles contained in the acetonitrile into products having different physical characteristics than acetonitrile and passing the acetonitrile through a series of adsorbent beds to remove the resulting products and other impurities in the acetonitrile.

DETAILED DESCRIPTION OF THE INVENTION

This invention is directed to a method for acetonitrile purification employing an adsorption-based process. The acetonitrile purification process comprises pretreating the acetonitrile containing organic impurities, such as unsaturated nitriles, by adding a solid reagent to selectively convert the unsaturated nitriles into products more easily removed, and passing the treated acetonitrile through a series of adsorbent beds to remove the resulting products and other impurities present from the acetonitrile.

The pretreatment step has three embodiments for the reagent used for the conversion of the unsaturated nitriles. The acetonitrile can be pretreated with a strong base, an oxidizing agent, or a polymerization initiator to selectively convert the unsaturated nitriles.

In one embodiment of the invention, the acetonitrile is pretreated with a strong base such as alkali hydroxides. In the process of this invention, the hydroxide catalyzes the condensation of the unsaturated nitriles to aromatic pyrimidines as well as initiating formation of some polymeric species. The use of solid alkali metal hydroxide, which is largely insoluble in acetonitrile, initiates reactions at the solid-liquid interface, facilitating the removal of the product impurities. The solid alkali metal hydroxide can also act as a bulk dehydrating agent. The unexpected advantages of this invention as practiced with solid alkali metal hydroxide as pretreatment reagent include remarkably low levels of hydrolysis and decomposition of acetonitrile, as compared with the use of aqueous base solutions, and resultant high product yields.

Suitable strong bases include, but are not restricted to, alkali metal hydroxides, basic aluminas, hydroxide ion-exchanged anion exchange resins, metal oxide catalysts such as chromium oxide/zinc oxide/aluminum oxide, other basic metal oxides, and mixtures thereof. Preferred strong bases are sodium hydroxide and potassium hydroxide, with potassium hydroxide particularly preferred.

The strong base is added to the acetonitrile in a batch or continuous process to provide an amount of base approximately 0.1 to 1000 moles per mole of total unsaturated nitrile, with 0.5 to 100 moles being preferred.

In another embodiment of the invention, a solid oxidizing agent is used as the reagent in the pretreatment step. The oxidizing agent selectively oxidizes the unsaturated nitriles to highly polarized materials which are readily removed by adsorption. The use of oxidizing agents as pretreatment reagents in the process of this invention shows unexpected advantages in that the use of alkali metal hydroxide as cocatalyst is not required and aqueous or alcoholic solutions of oxidizing agent are not required for effective removal of $C=C$ and $C=O$ containing materials. As the oxidizing agent reacts, the product manganese dioxide precipitates from solution, facilitating purification of product acetonitrile. In addition, laborious acid treatments and multiple distillation treatments are rendered unnecessary by the use of selective adsorbents for purification.

Suitable oxidizing agents include, but are not restricted to, potassium permanganate, organic peracids such as peracetic acid, trifluoroperacetic acid, perbenzoic acid, etc.; chromium trioxide and chromic acid; lead tetra-acetate; mercuric acid and mercury(II) acetate; selenium dioxide; sodium metaperiodate; osmium tetraoxide; ruthenium tetraoxide and sodium metaperiodate/ruthenium dioxide; alkali metal and alkaline earth hypochlorites; solid mixed metal oxidation catalysts, and mixtures thereof. Potassium permanganate is the preferred oxidizing agent. Alkali metal and alkaline earth hypochlorites are suitable oxidizing agents as listed above, but for applications in which trace amounts of chloride ion cannot be tolerated, they are not suited.

The oxidizing agent is added to the acetonitrile in a batch or continuous process to provide an amount of oxidizing agent approximately 0.1 to 5 moles per mole of $C=C$ and $C=O$ containing material, with 1.0 to 3.0 moles being particularly preferred. Oxygen or oxygen containing gas can optionally be sparged (bubbled) through the solution to accelerate the oxidation process.

Another embodiment of the invention includes pretreatment with solid polymerization initiators to selectively convert the unsaturated nitriles to either high polarity compounds or polymer. One advantage that results from the use of polymerization initiators as pretreatment reagents include rapid reaction rates. Another advantage is the formation of polymeric material from the UV-adsorbing material in the acetonitrile, such polymeric material being largely insoluble in the acetonitrile, thus making their removal by decantation, centrifugation, or filtration relatively easy and making the efficiency of adsorbent treatment of the acetonitrile relatively efficient when compared with procedures known in the art.

Suitable polymerization initiators are any which rapidly and selectively polymerize olefinic compounds and which are relatively unreactive with acetonitrile and other aliphatic nitriles. Examples of polymerization initiators include, but are not restricted to, azonitriles such as AIBN (azobis(isobutyronitrile)); alkyl, aryl, and acyl peroxides such as benzoyl peroxide; hydroperoxides and ketone peroxides; peresters and peroxycarbonates; alkali metal and alkaline earth persulfates, such as potassium persulfate; organic sulfonyl azides, and mixtures thereof. The preferred polymerization initiator is potassium persulfate.

The polymerization initiator is added to acetonitrile in a batch or continuous process to provide an amount of polymerization initiator approximately 0.1 to 5.0 moles per mole of $C=C$ or $C=O$ containing material, with 1.0 to 3.0 moles being particularly preferred.

Appropriate temperatures for any of the pretreatment steps are between about 0° C. and about 80° C., with temperatures between 0° C. and 70° C. being preferred, and temperatures between 0° C. and 30° being particularly preferred. The choice of temperature is dependent on the reagent. When a base or an oxidizing agent is used as the reagent, temperatures near ambient temperatures are preferred. Many polymerization initiators react by prior thermal decomposition to generate active initiator species, and a higher temperature is chosen to provide an adequate decomposition rate.

In a preferred mode, the pretreatment is carried out in the liquid phase in a stirred tank reactor or flow reactor. Reaction times are chosen to provide complete conversion of unsaturated impurities to adsorbable products. The reaction time is from 1 to 10 hours.

The pretreated acetonitrile is then either decanted or filtered as necessary to remove precipitate or delivered directly to the first of the adsorbent beds. Any other conventional means known in the art may be utilized to remove the precipitate.

After the pretreatment step is performed, the acetonitrile is passed through a series of adsorbent beds. The beds are specifically designed to remove the resulting products from the conversion of the unsaturated nitriles and the other impurities present after the pretreatment step. For example, activated charcoal will remove polymer and aromatics. Aluminas, silica, molecular sieves, and alumino-silicates will trap polar organic compounds such as amides and alcohols, as well as functioning as dehydrating agents. The adsorbents can either be regenerated or disposed of in accordance with the application.

Adsorption materials suitable for this invention are activated carbon, large pore zeolites, alumina, silica, alumino-silicates, and similar materials known to the art for selective adsorption of polar materials such as macroporous polymeric resins and the like, and molecular sieves known to the art for selective removal of water from organic materials such as 3A or 4A molecular sieves. The materials can be layered, mixed in the adsorbent beds, or used in pure form in separate adsorbent beds in any order which results in acetonitrile of required purity which is acetonitrile having a UV cutoff of less than 190 nm and containing less than 1 ppm of water.

The adsorption step can be carried out preferably as a continuous fixed bed process. The adsorbent beds can be operated at ambient temperature or at elevated or temperature as required, and with either upward or downward flow. Regeneration of the adsorbent materials will be carried out by known methods such as treatment with streams of dry inert gas such as nitrogen at elevated temperature. In a preferred mode, the adsorbent beds are regenerated by recycling the acetonitrile through the bed and elevating the temperature.

Final filtering of the processed acetonitrile using standard microfiltration technology removes fine particles acquired from the adsorbent materials to yield product meeting the most stringent purity standards.

The process of this invention increases efficiency, energy utilization, and the overall yield when compared with distillative methods, which require elevated temperatures and long processing times, and which provide relatively low yields of purified product. The high selectivity of adsorbent materials for removal of impurities makes the overall yield of acetonitrile unexpectedly high.

Specific Embodiments

The following examples illustrate the process in accordance with this invention for acetonitrile purification comprising a pretreatment step and an adsorption step. The following examples demonstrate, but do not limit the instant invention.

EXAMPLE 1

Purification of Acetonitrile via Base Digestion/Adsorption Process

An 8.0 liter batch reactor vessel equipped with stirrer and nitrogen inlet and outlet was filled with 4.0 liters of product acetonitrile containing 0.05% water and ppm levels of allyl alcohol, acrylonitrile, crotononitrile, and acetamide. To this was added 4.0 grams of dry potassium hydroxide powder (100-200 mesh). The resulting mixture was then stirred at 25° C. under nitrogen for 5 hours. The solution was then filtered and pumped through a fixed bed containing 100.0 cc of activated carbon, followed by a second bed containing 100 cc of Zeolite Type 13X available from UOP Inc. of Des Plaines, Ill., at a rate of 0.5 liters/hour, corresponding to an LHSV of 2.5 (v/v/hr). Final filtration through a microfiltration membrane removed fine particulate matter picked up from the adsorbent beds. The resulting acetonitrile was analyzed by gas chromatography. Karl Fisher Titration showed the acetonitrile to contain less than 30 ppm of water. Gas chromatography showed the acetonitrile to contain <0.1 ppm each of allyl alcohol, acrylonitrile, crotononitrile, and acetamide and has a UV cutoff of <190 nm. UV Gradient analysis yielded no peaks greater than 5 mAU at 210 nm.

EXAMPLE 2

Purification of Acetonitrile via Permanganate Oxidation/Adsorption Process

Solid potassium permanganate (0.1652 g, 1.05 mmol) was dissolved in a sample of acetonitrile (51.3 g) containing 5250 ppm water, 535 ppm acrylonitrile, 650 ppm crotononitrile (cis-trans mixture), and 570 ppm allyl alcohol. The solution was stirred at room temperature and monitored by gas chromatography. After 30 minutes a brown precipitate formed and the initial purple solution became clear and colorless. Additional potassium permanganate (0.1789 g, 1.13 mmol) was added, and the precipitation of brown solid was again complete after 60 minutes of additional stirring at room temperature, giving a colorless clear supernatant. Gas chromatography showed complete conversion of acrylonitrile and crotononitrile and 87% conversion of allyl alcohol. UV spectra of the starting material and product supernatant liquid showed dramatic decreases in UV absorption in the range of 190-300 nm after potassium permanganate pretreatment. Further addition of potassium permanganate was carried out to complete conversion of allyl alcohol.

The permanganate-treated acetonitrile is then passed over an adsorbent bed of activated carbon, followed by an adsorbent bed of Zeolite Type 13X available from UOP Inc. of Des Plaines, Ill., followed by an adsorbent bed of 3A molecular sieves. The product acetonitrile contains less than 30 ppm water and has a UV cutoff below 190 nm.

EXAMPLE 3

Purification of Acetonitrile via Selective Polymerization/Adsorption Process

Solid potassium persulfate (5 mmol) is added to a sample of acetonitrile (51.3 g) containing 5250 ppm water, 535 ppm acrylonitrile, 650 ppm crotononitrile (cis-trans mixture), and 570 ppm allyl alcohol. The solution is stirred at room temperature and monitored by gas chromatography. Gas chromatography shows substantial conversion of acrylonitrile, crotononitrile, and allyl alcohol. After filtration of the product solution, UV spectra of the starting material and product supernatant liquid shows dramatic decreases in UV absorption in the range of 190-300 nm after potassium persulfate treatment.

The persulfate-treated acetonitrile is then passed over an adsorbent bed of activated carbon, followed by an adsorbent bed of Zeolite Type 13X available from UOP Inc. of Des Plaines, Ill., followed by an adsorbent bed of 3A molecular sieves. The product acetonitrile contains less than 30 ppm of water and has a UV cutoff below 190 nm.

Although the invention has been described in detail through the proceeding examples, these examples are for the purpose of illustration only, and it is understood that variation and modifications can be made by one skilled in the art without departing from the spirit and scope of the invention.

What we claim is:

1. A process for the substantial removal of water and impurities from acetonitrile wherein at least one impurity is selected from the group consisting of acrylonitrile, crotonitrile and acetamide comprising
   a) adding a solid strong base to the acetonitrile in an amount sufficient to convert substantially all of said impurities into products which are capable of being easily separated from said acetonitrile by absorption
   b) passing the acetonitrile containing said products and water through a series of absorbent beds to separate said products and water from said acetonitrile thereby producing substantially pure acetonitrile and
   c) recovering said substantially pure acetonitrile from said absorbent beds.

2. A process for the substantial removal of water and impurities from acetonitrile wherein at least one impurity is selected from the group consisting of acrylonitrile, crotonitrile and acetamide comprising
   a) adding a solid polymerization initiator to the acetonitrile in an amount sufficient to convert substantially all of said impurities into products which are capable of being separated from said acetonitrile by absorption
   b) passing the acetonitrile containing said products and water through a series of absorbent beds to separate said products and water from said acetonitrile producing substantially pure acetonitrile and
   c) recovering said substantially pure acetonitrile from the absorbent beds.

3. The process for purifying acetonitrile of claim 1, wherein the strong base is selected from the group consisting of alkali metal hydroxides, basic aluminas, hydroxide ion-exchanged anion exchange resins, metal oxide catalysts, basic metal oxides, and combinations thereof.

4. The process for purifying acetonitrile of claim 1, wherein the strong base is selected from the group consisting of sodium hydroxide, potassium hydroxide, and combinations thereof.

5. The process for purifying acetonitrile of claim 1, wherein the strong base is potassium hydroxide.

6. The process for purifying acetonitrile of claim 1, wherein the strong base is added to the acetonitrile to provide an amount of base in the range of 0.1 to 1000 moles per mole of total unsaturated nitrile.

7. The process for purifying acetonitrile of claim 1, wherein the strong base is added to the acetonitrile to provide an amount of base in the range of 0.5 to 100 moles per mole of total unsaturated nitrile.

8. The process for purifying acetonitrile of claim 1, wherein the adsorbents are selected from the group consisting of activated carbon, large pore zeolites, alumina, silica, alumino-silicates, macroporous polymeric resins, and molecular sieves.

9. The process for purifying acetonitrile of claim 1, wherein the temperature for the pretreatment step is between 0° C. and about 80° C.

10. The process for purifying acetonitrile of claim 1, wherein the temperature for the pretreatment step is between 0° C. and about 70° C.

11. The process for purifying acetonitrile of claim 1 wherein the temperature for the pretreatment step is between 0° C. and about 30° C.

12. The process for purifying acetonitrile of claim 1, wherein the adsorption step is carried out as a continuous fixed bed process.

13. The process for purifying acetonitrile of claim 2, wherein the polymerization initiator is selected from the group consisting of azo-nitriles, alkyl peroxides, aryl peroxides, acyl peroxides, hydroperoxides, ketone peroxides, peresters, peroxycarbonates, alkali metal persulfates, alkaline earth persulfates, organic sulfonyl azides, and combinations thereof.

14. The process for purifying acetonitrile of claim 2, wherein the polymerization initiator is potassium persulfate.

15. The process for purifying acetonitrile of claim 2, wherein the polymerization initiator is added to the acetonitrile to provide an amount of initiator in the range of 0.1 to 5.0 moles per mole of unsaturated nitrile.

16. The process for purifying acetonitrile of claim 2, wherein the polymerization initiator is added to the acetonitrile to provide an amount of initiator in the range of 1.0 to 3.0 moles per mole of unsaturated nitrile.

* * * * *